(12) United States Patent
Bae et al.

(10) Patent No.: US 8,829,163 B2
(45) Date of Patent: Sep. 9, 2014

(54) LIQUID FORMULATIONS FOR LONG-ACTING ERYTHROPOIETIN CONJUGATE

(75) Inventors: Sung Min Bae, Seongnam-si (KR); Dae Seong Im, Yongin-si (KR); Min Young Kim, Suwon-si (KR); Chang Ki Lim, Hwaseong-si (KR); Sung Youb Jung, Suwon-si (KR); Se Chang Kwon, Seoul (KR)

(73) Assignee: Hanmi Science Co., Ltd, Hwaseong-si (KR)

( * ) Notice: Subject to any disclaimer, the term of this patent is extended or adjusted under 35 U.S.C. 154(b) by 0 days.

(21) Appl. No.: 13/574,029

(22) PCT Filed: Jan. 18, 2011

(86) PCT No.: PCT/KR2011/000370
§ 371 (c)(1),
(2), (4) Date: Jul. 19, 2012

(87) PCT Pub. No.: WO2011/090306
PCT Pub. Date: Jul. 28, 2011

(65) Prior Publication Data
US 2012/0296069 A1    Nov. 22, 2012

(30) Foreign Application Priority Data
Jan. 19, 2010    (KR) .................. 10-2010-0004840

(51) Int. Cl.
| | | |
|---|---|---|
| *A61K 39/00* | (2006.01) | |
| *C07K 16/00* | (2006.01) | |
| *A61K 47/02* | (2006.01) | |
| *A61K 47/26* | (2006.01) | |
| *A61K 47/48* | (2006.01) | |
| *A61K 47/18* | (2006.01) | |
| *A61K 9/00* | (2006.01) | |
| *A61K 47/10* | (2006.01) | |

(52) U.S. Cl.
CPC ............. *A61K 47/02* (2013.01); *A61K 47/26* (2013.01); *A61K 47/48507* (2013.01); *A61K 47/183* (2013.01); *A61K 47/48415* (2013.01); *A61K 9/0019* (2013.01); *A61K 47/10* (2013.01)
USPC ........................................ 530/387.3; 530/399

(58) Field of Classification Search
None
See application file for complete search history.

(56) References Cited

U.S. PATENT DOCUMENTS

| | | | |
|---|---|---|---|
| 4,992,419 A | 2/1991 | Woog et al. | |
| 2004/0087507 A1 | 5/2004 | Yamazaki et al. | |
| 2006/0269553 A1* | 11/2006 | Kim et al. ............ | 424/155.1 |
| 2009/0258017 A1* | 10/2009 | Callahan et al. ....... | 424/134.1 |

FOREIGN PATENT DOCUMENTS

| | | | |
|---|---|---|---|
| KR | 10-0610003 A | | 8/2006 |
| KR | 10-0725315 A | | 5/2007 |
| RU | 2268067 C2 | | 1/2006 |
| WO | WO 2004/006958 | * | 1/2004 |
| WO | 2004/108152 A1 | | 12/2004 |
| WO | 2005/014025 A1 | | 2/2005 |
| WO | 2005/047334 A1 | | 5/2005 |

OTHER PUBLICATIONS

International Search Report of PCT/KR2011/000370, dated Sep. 21, 2011.
Russian Patent Office, Russian Office Action issued in corresponding RU Application No. 2012135505, dated Aug. 19, 2013.

* cited by examiner

*Primary Examiner* — Elizabeth C Kemmerer
*Assistant Examiner* — Regina M Deberry
(74) *Attorney, Agent, or Firm* — Sughrue Mion, PLLC

(57) ABSTRACT

Disclosed is a liquid formulation which allows long-acting EPO conjugates, that have improved in vivo duration and stability, to be stable when stored for a long period of time. It comprises a stabilizer composition characterized by buffer and mannitol. Being free of human serum albumin and other potential factors harmful to the body, the liquid formulation is free of concerns about viral infections and guarantees excellent storage stability to long-acting EPO conjugates.

17 Claims, 2 Drawing Sheets

| No. | Salt | Stabilizer | Surfactant |
|---|---|---|---|
| #1 | 200mM NaCl | 10% Maltose | 0.005% polysorbate 80 |
| #2 | 200mM NaCl | 10% Maltose, 1% Glycine | 0.005% polysorbate 80 |
| #3 | 200mM NaCl | 10% Mannitol | 0.005% polysorbate 80 |
| Recormon | | | |

LIQUID FORMULATIONS FOR LONG-ACTING ERYTHROPOIETIN CONJUGATE

CROSS REFERENCE TO RELATED APPLICATIONS

This application is a National Stage of International Application No. PCT/KR2011/000370 filed Jan. 18, 2011, claiming priority based on Korean Patent Application No. 10-2010-0004840 filed Jan. 19, 2010, the contents of all of which are incorporated herein by reference in their entirety.

TECHNICAL FIELD

The present invention relates to a liquid formulation for guaranteeing long-term storage stability of a long-acting erythropoietin conjugate in which erythropoietin, a non-peptide polymer and an immunoglobulin Fc fragment are covalently linked and which exhibits an extended duration of action compared to the wild-type.

BACKGROUND ART

Erythropoietin (EPO) is a glycoprotein, consisting of 165 amino acid residues, which acts as a cytokine for erythrocyte precursors in the bone marrow, thus being responsible for controlling erythropoiesis (red blood cell production). EPO is synthesized mainly by renal cells, with a small amount being produced by the liver. As seen in chronic renal failure, the loss of renal functions typically is accompanied by a decrease, for example, in EPO level, with a concomitant decrease in erythrocyte production. Now, EPO is used to treat anemia resulting from chronic kidney disease and from other critical illnesses as well as being administered to patients scheduled to undergo surgery (Mijake et al., J. Biol. Chem. 25: 5558-5564, 1977; Eschbach et al., New Engl. J. Med. 316: 73-78, 1987; Sanford B. K, Blood, 177: 419-434, 1991; PCT WO 85-02610).

Human urinary EPO was first purified from patients with aplastic anemia by Miyake et al. (Miyake et al., J. Biol. Chem., 252: 5558, 1977), but the amount of EPO from this source is insufficient for use in the treatment of anemia. Since the publication of U.S. Pat. No. 4,703,008 disclosing the identification and cloning of a human EPO gene and the expression of recombination EPO proteins, the mass production of EPO has been achieved by various different genetic manipulations.

Since polypeptides tend to easily denature due to their low stability, be degraded by proteolytic enzymes in the blood and easily passed through the kidney or liver, protein medicaments, including polypeptides as pharmaceutically effective components, need to be frequently administered to patients to maintain the desired blood level concentrations and titers. However, this frequent administration of protein medicaments, especially by injection, causes pain in patients.

To solve these problems, a lot of effort has been put into improving the serum stability of protein drugs and maintaining the drugs in the blood at high levels for a prolonged period of time, and thus maximizing the pharmaceutical efficacy of the drugs. For use in long-acting formulations, protein drugs must be formulated to have high stability and have their titers maintained at sufficiently high levels without incurring immune responses in patients.

To stabilize proteins and prevent enzymatic degradation and clearance by the kidneys, a polymer having high solubility, such as polyethylene glycol (PEG), was conventionally used to chemically modify the surface of a protein drug. By binding to specific or various regions of a target protein, PEG stabilizes the protein and prevents hydrolysis, without causing serious side effects (Sada et al., J. Fermentation Bioengineering 71:137-139, 1991). However, despite its capability to enhance protein stability, PEGylation has problems such as greatly reducing the titers of physiologically active proteins. Further, the yield decreases with increasing molecular weight of the PEG due to the reduced reactivity of the proteins.

An alternative method for improving the in vivo stability of physiologically active proteins is by linking a gene of a physiologically active protein to a gene encoding a protein having high serum stability by genetic recombination technology and culturing the cells transfected with the recombinant gene to produce a fusion protein. For example, a fusion protein can be prepared by conjugating albumin, a protein known to be the most effective in enhancing protein stability, or its fragment to a physiologically active protein of interest by genetic recombination (PCT Publication Nos. WO 93/15199 and WO 93/15200, European Pat. Publication No. 413,622).

Another method is to use an immunoglobulin. As described in U.S. Pat. No. 5,045,312, human growth hormone is conjugated to bovine serum albumin or mouse immunoglobulin by use of a cross-linking agent. The conjugates have enhanced activity when compared with unmodified growth hormone. Carbodiimide or glutaraldehyde is employed as the cross-linking agent. Non-specifically bonding to the peptides, however, such low-molecular weight cross-linking agents do not allow the formation of homogeneous conjugates and are even toxic in vivo. In addition, the patent shows activity enhancement only thanks to chemical coupling with the growth hormone. The method of the patent cannot guarantee activity enhancement to various kinds of polypeptide drugs, so that the patent does not recognize even protein stability-related factors, such as duration, blood half-period, etc.

Recently a drug formulation has been suggested that is a long-acting protein drug formulation with improvement in both in vivo duration and stability. For use in the long-acting drug formulation, a protein conjugate is prepared by covalently linking a physiologically active polypeptide, a non-polypeptide polymer and an immonoglobulin Fc fragment (Korean Patent No. 10-0567902 and 10-0725315).

In this method, EPO can be used as a physiologically active polypeptide to afford a long-acting EPO conjugate. To apply long-acting EPO conjugates to drug products, it is necessary to maintain the pharmaceutical efficacy thereof in vivo while restraining physicochemical changes such as light-, heat- or additives-induced degeneration, aggregation, adsorption or hydrolysis during storage and transportation. Long-acting EPO conjugates are more difficult to stabilize than an EPO polypeptide itself because they are increased in volume and molecular weight.

Generally, proteins have a very short half life and, when exposed to unsuitable temperatures, water-air interfaces, high pressures, physical/mechanical stress, organic solvents, microbial contamination, etc., they undergo such degeneration as the aggregation of monomers, precipitation by aggregation, and adsorption onto the surface of containers. When degenerated, proteins lose their physicochemical properties and physiological activity. Once degenerated, proteins almost cannot recover their original properties because the degeneration is irreversible. Particularly in the case of the proteins that are administered in trace amounts of hundreds migrograms per injection, such as EPO, when they lose stability and thus are absorbed onto the surface of the container, a relatively great amount of damage results. In addition, absorbed proteins easily aggregate during a degeneration process, and aggregates of the degenerated proteins, when administered into the body, act as antigens, unlike proteins synthesized in vivo. Thus, proteins must be administered in a stable form. Many studies have been done to prevent the degeneration of proteins in solutions (John Geigert, J. Parenteral Sci. Tech., 43(5): 220-224, 1989; David Wong, Pharm. Tech., 34-48, 1997; Wei Wang., Int. J. Pharm., 185: 129-188, 1999; Willem Norde, Adv. Colloid Interface Sci., 25: 267-340, 1986; Michelle et. Al., Int. J. Pharm. 120: 179-188, 1995).

Lyophilization is applied to some protein drugs to achieve the goal of stability. However, lyophilized products are inconvenient in that they must be re-dissolved in injection water for use. In addition, they need massive investment on large-capacity freeze-driers because lyophilization process is included in the production processes thereof. The confrication of proteins by use of a spray drier was suggested. However, this method is economically unfavorable due to low production yield. Further, a spray-drying process exposes the proteins to high temperatures, thus having negative influences on the stability of the proteins.

As an alternative to overcome the limitations, stabilizers have appeared that, when added to proteins in solution, can restrain physicochemical changes of protein drugs and maintain in vivo pharmaceutical efficiency even after having been stored for a long period of time. Among them are carbohydrates, amino acids, proteins, surfactants, polymers and salts. Inter alia, human serum albumin has been widely used as a stabilizer for various protein drugs, with certification for its performance (Edward Tarelli et al., Biologicals, 26: 331-346, 1998).

A typical purification process for human serum albumin includes inactivating biological contaminants such as mycoplasma, prion, bacteria and virus or screening or examining one or more biological contaminants or pathogens. However, there is always the risk that patients are exposed to the biological contaminants because they are not completely removed or inactivated. For example, human blood from donors is screened to examine whether it contains certain viruses. However, this process is not always reliable. Particularly, certain viruses existing in a very small number cannot be detected.

Alternatives to human serum albumin have recently been suggested, including recombinant albumin (Korean Patent Laid-Open Publication No. 10-2004-0111351) and albumin-free erythropoietin (Korean Patent Nos. 10-0560697 and 10-0596610).

Although employing stabilizers free of albumin, different proteins may be gradually inactivated due to the chemical differences thereof because they are subjected to different ratios and conditions during storage. The effect of a stabilizer on the storage term of proteins differs from one protein to another. That is, various stabilizers may be used at different ratios depending on physicochemical properties of the proteins of interest.

In addition, different stabilizers, when concurrently used, may bring about reverse effects due to competition and the erroneous operation thereof. A combination of different stabilizers also elicits different effects because they cause the proteins to change in characteristics or concentration during storage. Because each stabilizer suitably performs its stabilizing activity in a certain range of concentrations, many efforts must be made to combine the kinds and concentrations of different stabilizers, with care.

Particularly for long-acting EPO conjugates which have improved in vivo duration and stability, their molecular weights and volumes are quite different from those of general erythropoietin compounds because they are composed of the physiologically active peptide EPO, non-peptide polymers and the immunoglobulin Fc fragment. Accordingly, stabilizers with special compositions different from those of stabilizers of EPO are required for long-acting EPO conjugates.

Leading to the present invention, intensive and thorough research into the development of a stable liquid formulation for long-acting EPO conjugates, capable of retaining pharmaceutical efficacy for a long period of time without viral infection, resulted in the finding that a stabilizer comprising a buffer and a high concentration of mannitol endows long-acting EPO conjugates with enhanced stability and allows the formation of economical and stable liquid formulations of long-acting EPO conjugates.

DISCLOSURE

Technical Problem

It is therefore an object of the present invention to provide a liquid formulation comprising a long-acting erythropoietin conjugate in which EPO, a non-peptide polymer and an immunoglobulin Fc fragment are covalently linked, and an albumin-free stabilizer composed of buffer and mannitol.

Technical Solution

In accordance with an embodiment thereof, the present invention provides a liquid formulation comprising a long-acting erythropoietin conjugate in which EPO, a non-peptide polymer and an immunoglobulin Fc fragment are covalently linked, and an albumin-free stabilizer composed of buffer and mannitol.

The term "long-acting erythropoietin conjugate" or "long-acting EPO conjugate", as used herein, is intended to refer to a protein construct in which the physiologically active EPO, one or more non-peptide polymers and one or more immunoglobulin Fc fragments are covalently linked, and which has a prolonged duration of action compared to EPO in its natural form.

The term "long-acting", as used herein, refers to a prolonged duration of action compared to that of a natural form. The term "conjugate" refers to a construct in which EPO, a non-peptide polymer and an immunoglobulin Fc fragment are covalently linked.

For use in the present invention, the EPO has an amino acid sequence of human erythropoietin or closely related analogues. The EPO useful in the present invention may be a naturally occurring protein or a recombinant protein. Also, the EPO may be a mutant one that has undergone the insertion, deletion or insertion of amino acids provided that the mutation does not have a significant influence on the original biological activity thereof.

Human EPO or its analogues useful in the present invention may be isolated from vertebrates or may be chemically synthesized. Alternatively, EPO or its analogues may be obtained from prokaryotes or eukaryotes which are transformed with a gene encoding EPO or its analogue using a genetic recombination technique. In this regard, colon bacteria (e.g., *E. coli*), yeast cells (e.g., *S. cerevisiae*), or mammalian cells (e.g., Chinese hamster ovarian cells, monkey cells) may be used as host cells. Depending on the host cells, the recombinant EPO or its analogues may be glycosylated with mammalian or eukaryotic carbohydrates or aglycosylated. When expressed, the recombinant EPO or its analogues may contain the initial methionine residue (position −1). Preferably, recombinant human EPO (HuEPO) is prepared using CHO cells as a host.

For use in the present invention, the immunoglobulin Fc fragment has an amino acid sequence of human immunoglobulin Fc fragments or their closely related analogues. The Fc fragments may be obtained from native forms isolated from animals including cows, goats, swine, mice, rabbits, hamsters, rats and guinea pigs. In addition, the immunoglobulin Fc fragment may be an Fc fragment that is derived from IgG, IgA, IgD, IgE and IgM, or that is made by combinations thereof or hybrids thereof. Preferably, it is derived from IgG or IgM, which is among the most abundant proteins in human blood, and most preferably from IgG, which is known to enhance the half-lives of the ligand-binding proteins. Herein, the immunoglobulin Fc may be obtained from a native immunoglobulin by isolating whole immunoglobulins from human or animal organisms and treating them with a proteolytic enzyme or it may be recombinants or derivatives thereof, obtained from transformed animal cells or microorganisms. Preferable is recombinant human immunoglobulin Fc produced by E. coli transformants.

On the other hand, IgG is divided into IgG1, IgG2, IgG3 and IgG4 subclasses, and the present invention includes combinations and hybrids thereof. Preferred are IgG2 and IgG4 subclasses, and most preferred is the Fc fragment of IgG4 rarely having effector functions such as CDC (complement dependent cytotoxicity). That is, as the drug carrier of the present invention, the most preferable immunoglobulin Fc fragment is a human IgG4-derived aglycosylated Fc fragment. The human-derived Fc fragment is more preferable than a non-human derived Fc fragment, which may act as an antigen in the human body and cause undesirable immune responses such as the production of a new antibody against the antigen.

The long-acting EPO conjugate useful in the present invention is prepared by linking the EPO and the immunoglobulin Fc fragment together. In this regard, the EPO and the immunoglobulin Fc fragment may be cross-linked via a non-peptide polymer or may be formed into a fusion protein using a recombinant technique.

The non-peptide polymer for use in cross-linking may be selected from the group consisting of biodegradable polymers, lipid polymers, chitins, hyaluronic acid, and combinations thereof. The biodegradable polymer may be selected from polyethylene glycol, polypropylene glycol, copolymers of ethylene glycol and propylene glycol, polyoxyethylated polyols, polyvinyl alcohol, polysaccharides, dextran, polyvinyl ethyl ether, PLA (poly(lactic acid), PLGA (polylactic-glycolic acid), and combinations thereof. Most preferred is poly(ethylene glycol) (PEG), with a preference for polyethylene glycol. Also, derivatives thereof well known in the art and able to be easily prepared within the skill of the art are included in the scope of the present invention.

The long-acting EPO conjugates useful in the present invention may be prepared using a genetic engineering technique, as disclosed in Korean Patent No. 10-0725315.

The liquid formation according to the present invention comprises a long-acting EPO conjugate in a therapeutically effective amount. Typically, the therapeutically effective amount of EPO ranges from 2,000 to 10,000 international units (IU) per single-use vial. The concentration of the long-acting EPO conjugates used in the present invention is on the order of 1 to 5000 μg/ml, and preferably on the order of 50 to 3000 μg/ml.

As used herein, the term "stabilizer" is intended to refer to a substance which allows the long-acting EPO conjugate to be safely stored. The term "stabilization" is intended to mean the loss of an active ingredient by up to a predetermined rate, generally, up to 10%, for a certain period of time under a storage condition. When EPO retains 90% or more of its original activity and preferably 95% or higher of the original activity after having been stored at 10° C. for 2 years, at 25° C. for 6 months or at 40° C. for one to two weeks, it is understood as being stable. As for proteins such as EPO, their storage stability is important in suppressing the potential generation of EPO-like antigenic materials as well as guaranteeing accurate administration amounts. During storage, about 10% loss of EPO activity may be understood as being permissible for administration unless EPO within the formulation aggregates or is fragmented to form antigenic materials.

The stabilizer suitable for use in the present invention comprises a buffered solution formulated to endow the long-acting EPO conjugate with stability, and mannitol.

In addition, the stabilizer according to the present invention is preferably free of albumin. Because it is prepared from human blood, human serum albumin, available as a stabilizer for proteins, has the possibility of being contaminated by human-derived pathogenic viruses. Gelatin or bovine serum albumin may cause diseases or induce an allergic reaction in some patients. Free of human- or animal-derived serum albumin or heterogeneous proteins such as purified gelatin, the stabilizer according to the present invention is freed from concerns about viral infection.

Mannitol, a kind of sugar alcohol, is used in the stabilizer of the present invention because it acts to enhance the stability of the long-acting EPO conjugate. Mannitol is used preferably at a concentration of from 1 to 20% (w/v) based on the total volume of the liquid formulation, more preferably at a concentration of from 3 to 12% (w/v) and most preferably at a concentration of from 5 to 10% (w/v).

In accordance with an embodiment of the present invention, when mannitol in the presence of a phosphate buffered solution was used as a stabilizer, the storage stability of the long-acting EPO conjugate was shown to increase more greatly than when conventional stabilizers including sorbitol, maltose, PEG400 and amino acids were used (see Table 1). When applied to the present invention, maltose, used as a stabilizer in Japanese Patent Laid-Open Publication No. 2009-249292, was found to decrease the stability of the long-acting EPO conjugate as the storage term was extended (see Table 8).

These data reveal the specificity of mannitol as a stabilizer for the long-acting EPO conjugate, compared to other stabilizers, indicating that different stabilizers are needed according to the targets in need of stabilization.

The buffer solution in the stabilizer plays a role in keeping the pH of the liquid formulation constant to prevent fluctuations in the pH, thus stabilizing the long-acting EPO conjugate. The buffer solution useful in the present invention may comprise pharmaceutically acceptable pH buffering agents including alkaline salts (sodium or potassium phosphate, hydrogen or dihydrogen salts thereof), sodium citrate/citric acid, sodium acetate/acetic acid, and a combination thereof. Suitable for use in the present invention is citrate buffer, phosphate buffer, tartarate buffer, carbonate buffer, succinate buffer, lactate buffer and acetate buffer, with a preference for phosphate buffer and citrate buffer, phosphate buffer being greater preferred. In phosphate buffer, phosphate ranges in concentration preferably from 5 to 100 mM and more preferably from 10 to 50 mM. The buffer has preferably a pH of 4.0 to 8.0 and more preferably a pH of 5.0 to 7.0.

In another embodiment of the present invention, the stabilizer useful in the present invention may further comprise at least one component selected from the group consisting of isotonic agents, polyhydric alcohols, sugars, non-ionic surfactants and neutral amino acids, in addition to the buffer solution and mannitol.

The isotonic agent acts not only to maintain a suitable osmotic pressure when the long-acting EPO conjugate in the liquid formulation is allowed to enter the body, but to further stabilize the long-acting EPO conjugate in the liquid formation. Examples of the isotonic agent include water-soluble inorganic salts. Among them are sodium chloride, sodium sulfate, sodium citrate, calcium chloride, and a combination thereof. Most preferable is sodium chloride.

Preferably, the concentration of the isotonic agent is on the order of 5 to 200 mM. Within this range, the concentration of the isotonic may be adjusted according to the kinds and amounts of the components contained such that the liquid formulation is isotonic.

According to an embodiment of the present invention, the influence on the stability of the long-acting EPO conjugate in the presence of a buffer solution was evaluated for various kinds of salts. As a result, liquid formulations which comprise sodium sulfate, sodium chloride, sodium citrate or a combination of sodium sulfate and sodium chloride, together with a phosphate buffered solution, were found to increase the stability of the long-acting EPO conjugate, compared to the liquid formulations free of salts (see Table 2). From the data, it is understood that the long-acting EPO conjugate of the present invention is stabilized to different extents depending on the kinds of salts used and shows a peak stability with some salts.

Preferred examples of the sugar which can be further contained to increase the storage stability of the long-acting EPO conjugate include monosaccharides such as mannose, glucose, fucose and xylose, and polysaccharides such as lactose, maltose, sucrose, raffinose and dextran. In the liquid formulation, the sugar is preferably used in an amount of from 1 to 20% (w/v) and more preferably used in an amount of from 5 to 20% (w/v). Examples of the polyhydric alcohol useful in the present invention include propylene glycol, low-molecular weight polyethylene glycol, glycerol, and low-molecular weight polypropylene glycol. They may be used alone or in combination. And their concentration in the liquid formulation is preferably on the order of 1 to 15% (w/v) and more preferably on the order of 5 to 15% (w/v).

As for the non-ionic surfactant, it lowers the surface tension of the protein solution to prevent the proteins from being adsorbed onto or aggregating at hydrophobic surfaces. polysorbate-based non-ionic surfactants and poloxamer-based non-ionic surfactants are suitable for use in the present invention. They may be used alone or in combination. Preferred is polysorbate-based non-ionic surfactants. Among them are polysorbate 20, polysorbate 40, polysorbate 60 and polysorbate 80, with greater preference for polysorbate 80.

It is not recommended to use the non-ionic surfactant in a high concentration because the non-ionic surfactant, if present at a high concentration, induces interference with UV-spectrometry or iso-focusing to make it difficult to evaluate the concentration or stability of protein, accurately. Thus, the liquid formulation of the present invention may comprise the non-ionic surfactant preferably at a concentration of 0.1% (w/v) or less and more preferably at a concentration of from 0.001 to 0.05% (w/v).

In an embodiment of the present invention, non-ionic surfactants were analyzed for effect on the stability of protein in the presence of phosphate buffer. During a storage term of as short as one week, the non-ionic surfactants were found to have little influence on the stability of the long-acting EPO conjugate (see Table 3). Also, when the non-ionic surfactant polysorbate 80 was used, the long-acting EPO conjugate was found to be more stabilized during storage by a stabilizer containing 0.01% polysorbate 80 than 0.1% polysorbate 80 (see Table 4).

An amino acid, also available as a stabilizer for the liquid formulation, acts to attract more water molecules around EPO in a solution, so that the outermost hydrophilic amino acid molecules of the EPO are further stabilized (Wang, Int. J. Pharm. 185: 129-188, 1999). In this regard, charged amino acids may induce electrostatic attraction with EPO to promote the aggregation of EPO. Hence, neutral amino acids, such as glycine, alanine, leucine and isoleucine, are added as a stabilizing component. In the liquid formulation, the neutral amino acid is used preferably at a concentration of from 0.1 to 10% (w/v).

In an embodiment of the present invention, maltose guaranteed higher storage stability to long-acting EPO conjugates when used in combination with glycine than alone. However, treatment with mannitol at a concentration of as high as 3 to 12% (w/v) was observed to provide higher stability even in the absence of neutral amino acids than treatment with a combination of maltose and glycine (see Table 10).

Accordingly, a liquid formulation for providing high stability for long-acting EPO conjugates can be prepared using a high concentration of mannitol even when no neutral amino acids are added. However, a mannitol concentration exceeding 20% (w/v) is out of the upper isotonic limit. Thus, mannitol is used at a concentration of from 1 to 20% in the liquid formulation, preferably at a concentration of from 3 to 12% (w/v), and more preferably at a concentration of from 5 to 10% (w/v).

In addition to the above-mentioned components including a buffer, an isotonic agent, a sugar alcohol, a neutral amino acid and a non-ionic surfactant, the liquid formulation of the present invention may further selectively comprise other components known in the art so long as they do not deteriorate the effect of the present invention.

According to a preferred embodiment of the present invention, the liquid formulation does not contain albumin and may comprise a buffer solution, mannitol, an isotonic agent and a non-ionic surfactant.

In greater detail, the present invention provides a liquid formulation which comprises a long-acting EPO conjugate, and a stabilizer, the stabilizer comprising phosphate or citrate buffer, mannitol, an isotonic agent and polysorbate 80, the isotonic agent being selected from the group consisting of sodium chloride, sodium sulfate, sodium citrate and a combination thereof. Preferably, the liquid formulation comprises a phosphate or citrate buffer solution at a concentration of from 5 to 100 mM, mannitol at a concentration of from 1 to 20% (w/v), an isotonic agent at a concentration of from 5 to 200 mM, the isotonic agent being selected from the group consisting of sodium chloride, sodium sulfate and sodium citrate, and polysorbate 80 at a concentration of from 0.001 to 0.05% (w/v). More preferably, the liquid formula comprises a phosphate buffer solution at a concentration of from 5 to 100 mM, mannitol at a concentration of from 3 to 12% (w/v), sodium chloride at a concentration of from 100 to 200 mM, and polysorbate 80 at a concentration of from 0.001 to 0.05% (w/v). Most preferably, the liquid formulation comprises a sodium phosphate buffer (pH 6.5) at a concentration of 10 mM, mannitol at a concentration of from 5 to 10% (w/v), sodium at a concentration of from 100 to 200 mM, and polysorbate 80 at a concentration of from 0.001 to 0.05% (w/v), and comprises no neutral amino acids.

In an embodiment of the present invention, a liquid formulation for long-acting EPO conjugates comprising a sodium-phosphate buffer solution at a concentration of 10 mM (pH 6.5), mannitol at a concentration of from 5 to 10% (w/v), sodium chloride at a concentration of from 100 to 200 mM and polysorbate 80 at a concentration of from 0.001 to 0.05% (w/v) was compared with the known EPO formulation Recormon, Roche, for the storage stability of EPO. EPO was found to be more stable in the liquid formulation of the present invention than in the commercially available one (see Tables 6 and 14).

Also, the liquid formulation for EPO according to the present invention was compared with other formulations, such as Aranesp, a therapeutic for anemia manufactured by Amgen, Enbrel (TNFR-Fc), a therapeutic for rheumatoid arthritis manufactured by Amgen, and PBS alone, for the storage stability of EPO. As a result, the liquid formulation for long-acting EPO conjugates according to the present invention exhibited higher stability than any other liquid formulation (see Table 17).

In another embodiment, the liquid formulation for long-acting EPO conjugates in accordance with the present invention was assayed for long-term stability and found to keep the long-acting EPO conjugates stably for 12 months and guaranteed at least 92.5% of the activity even after 6 months of storage under an accelerated condition (see Tables 19 to 21).

From the data, it is understood that the liquid formulation comprising buffer and mannitol at a concentration of from 1 to 20% (w/v) can store long-acting EPO conjugate therein stably for 12 months or longer even in the absence of neutral amino acids.

Advantageous Effects

Being free of human serum albumin and other potential factors harmful to the body, the liquid formulation for long-acting erythropoietin conjugates in accordance with the present invention is freed from concerns about viral infections and guarantees excellent storage stability to the long-acting EPO conjugates in which EPO and immunoglobulin Fc fragment are linked and which are greater in molecular weight and longer in the duration of action than natural forms of EPO. Even when containing no neutral amino acids, the liquid formulation of the present invention can provide excellent storage stability for EPO, thus being economically more beneficial than other stabilizers and lyophilizing agents.

MODE FOR INVENTION

Figure 1:
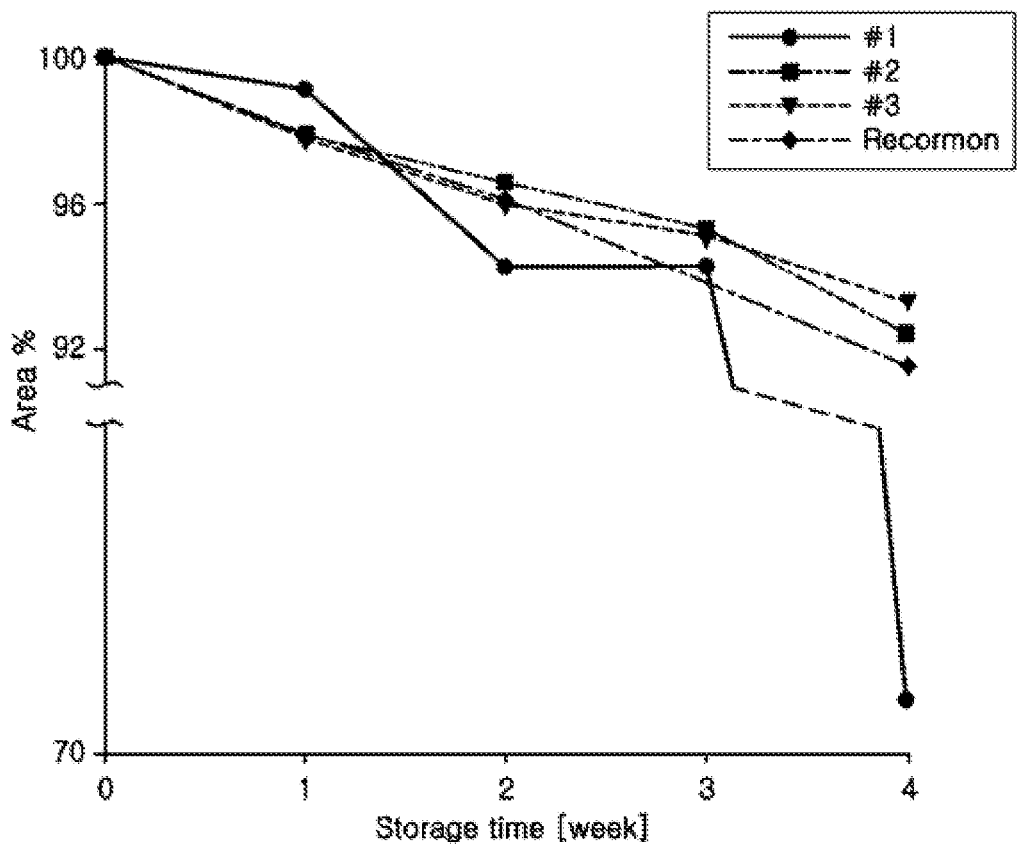
FIG. 1 is a graph showing the stability of EPO in different liquid formulations for long-acting EPO conjugate and in the commercially available EPO formulation Recormon when they are analyzed using reverse-phase chromatography every week for the duration of storage at 40° C. for four weeks.

A better understanding of the present invention may be obtained through the following examples which are set forth to illustrate, but are not to be construed as limiting the present invention.

Example 1

Construction of Long-Acting EPO Conjugate

<1-1> Preparation of Immunoglobulin Fc Fragment Using Immunoglobulin

The immunoglobulin Fc fragment useful in the present invention was human aglycosylated IgG4 Fc fragment which could be expressed from the E. coli transformant as disclosed in Korean Patent No. 725314.

<1-2> Preparation of Recombinant Human Erythropoietin

The human EPO used in this example was obtained as disclosed in Korean Patent No. 880509. For this, an animal cell line transformed with a vector capable of greatly enhancing gene amplification efficiency by artificially weakening a dihydrofolate reductase gene promoter, which is a transcriptional control sequence of the gene, was cultured to express human EPO proteins. Only highly glycosylated proteins were purified for use.

<1-3> Preparation of Long-Acting EPO Conjugate Using Immunoglobulin Fc Fragment

The long-acting EPO conjugate in this example was a construct in which a human erythropoietin and an immunoglobulin Fc fragment is covalently linked by a non-peptide polymer. And it was obtained as disclosed in Korean Patent No. 725315 and 775343.

Example 2

Assay of Long-Acting EPO Conjugates for Stability According to Various Stabilizers In the presence of phosphate buffer, various stabilizing agents including sugars, sugar alcohols, polyhydric alcohols and amino acids were assayed for their ability to stabilize the long-acting EPO conjugate.

For the assay, Na-phosphate buffer was used as a phosphate buffer, mannitol or sorbitol as a sugar alcohol, histidine or methionine as a sugar alcohol, maltose as a sugar, and PEG 400 as a polyhydric alcohol.

After storage at 40° C. for one week in the compositions listed in Table 1, reverse phase chromatography was performed to conduct analysis. The results are summarized in Table 1, below. The retention rate of the long-acting EPO conjugate compared to the initial value thereof was expressed as RPC (%) (area %/initial area %).

TABLE 1

| No. | EPO | Buffer | Stabilizing agent | RPC (%) |
|---|---|---|---|---|
| 1 | 200 µg/ml | 10 mM Na-Phosphate, pH 6.5 | 1% Mannitol | 95.2 |
| 2 | 200 µg/ml | 10 mM Na-Phosphate, pH 6.5 | 1 mM Histidine | 86.2 |
| 3 | 200 µg/ml | 10 mM Na-Phosphate, pH 6.5 | 1 mM Methionine | 76.1 |

TABLE 1-continued

| No. | EPO | Buffer | Stabilizing agent | RPC (%) |
|---|---|---|---|---|
| 4 | 200 μg/ml | 10 mM Na-Phosphate, pH 6.5 | 10% Maltose | 93.5 |
| 5 | 200 μg/ml | 10 mM Na-Phosphate, pH 6.5 | 1% PEG 400 | 92.8 |
| 6 | 200 μg/ml | 10 mM Na-Phosphate, pH 6.5 | 1% Sorbitol | 92.7 |

As is apparent from the data of Table 1, the use of mannitol as a stabilizing agent kept the long-acting EPO conjugate the most stable.

Example 3

Assay of Long-Acting EPO Conjugates for Stability According to Salts

In the presence of phosphate buffer, various salts were assayed for ability to stabilize the long-acting EPO conjugate, as follows. Salts such as alkaline salts and inorganic salts not only serve as pH buffering agents to endow the long-acting conjugate with additional pH stability, but as isotonic agents to maintain proper osmotic pressures.

After storing at 40° C. for one week the compositions listed in Table 2, reverse phase chromatography was preformed for analysis. For the assay, sodium phosphate buffer (pH 6.5) was used as a buffer while copper (II) chloride, sodium sulfate, sodium citrate and sodium carbonate were used as salts. The results are summarized in Table 2, below. The retention rate of the long-acting EPO conjugate compared to the initial value thereof was expressed as RP-HPLC (%).

TABLE 2

| No. | EPO | Buffer | Salt | RP-HPLC (%) |
|---|---|---|---|---|
| 1 | 200 μg/ml | 10 mM Na-Phosphate, pH 6.5 | — | 94.6 |
| 2 | 200 μg/ml | 10 mM Na-Phosphate, pH 6.5 | 30 mM CuCl$_2$ | 81.6 |
| 3 | 200 μg/ml | 10 mM Na-Phosphate, pH 6.5 | 40 mM Na$_2$SO$_4$ | 98.1 |
| 4 | 200 μg/ml | 10 mM Na-Phosphate, pH 6.5 | 200 mM NaCl | 97.0 |
| 5 | 200 μg/ml | 10 mM Na-Phosphate, pH 6.5 | 10 mM Na-Citrate | 97.5 |
| 6 | 200 μg/ml | 10 mM Na-Phosphate, pH 6.5 | 10 mM Na$_2$CO$_3$ | 83.2 |
| 7 | 200 μg/ml | 10 mM Na-Phosphate, pH 6.5 | 20 mM Na$_2$SO$_4$/100 mM NaCl | 97.7 |

As is apparent from the data of Table 2, the stability of the long-acting EPO conjugate was increased when sodium sulfate, sodium chloride, sodium citrate or a combination of sodium sulfate and sodium chloride was used in the presence of phosphate buffer, compared to the control to which none of them were added. In contrast, the stability of the long-acting EPO conjugate was decreased in the presence of copper (II) chloride, compared to the control.

From the data, it is understood that the long-acting EPO conjugate of the present invention is stabilized to different extents depending on the kinds of salts used and shows higher stability with some salts.

Example 4

Assay of Long-Acting EPO Conjugates for Stability According to Non-Ionic Surfactant In the presence of phosphate buffer, various non-ionic surfactants were assayed for ability to stabilize the long-acting EPO conjugate, as follows.

For the assay, polysorbate 80 was used as a non-ionic phosphate buffer, and other agents shown to provide stability for the long-acting EPO conjugate, including salts, sugar alcohols and sugars, were employed in proper combination.

For simplicity, sodium chloride was selected from among the verified salts including sodium chloride, sodium sulfate and sodium citrate. Also, mannitol proven in Example 1 as guaranteeing the most stability was used. Under the same condition that EPO was set to have 200 μg/ml in 10 mM sodium phosphate buffer (pH 6.5), the long-acting EPO conjugate of the present invention was stored at 40° C. for one week in the compositions listed in Table 3, followed by analysis by reverse phase chromatography. The results are summarized in Table 3, below. The retention rate of the long-acting EPO conjugate compared to the initial value thereof was expressed as RP-HPLC (%).

TABLE 3

| No. | Surfactant | Salt | Stabilizing Agent | RP-HPLC (%) |
|---|---|---|---|---|
| 1 | — | 100 mM NaCl | 10% Mannitol | 96.5 |
| 2 | 0.005% polysorbate 80 | 100 mM NaCl | 10% Mannitol | 97.8 |

Under the condition of the phosphate buffer, as seen in Table 3, the EPO did fluctuate a little in stability irrespective of the presence of the non-ionic surfactant, indicating that the non-ionic surfactant does have significant effects on the stability of EPO during as short as one week.

Also, an examination was made of the effect of the concentration of non-ionic surfactant on the stability of long-acting EPO conjugate. Under the same conditions that EPO was set to have 200 μg/ml in 10 mM sodium phosphate buffer (pH 6.5), the long-acting EPO conjugate of the present invention was stored at 40° C. for two weeks in the compositions listed in Table 4, followed by analysis by reverse phase chromatography. The results are summarized in Table 4, below. The retention rate of the long-acting EPO conjugate compared to the initial value thereof was expressed as RP-HPLC (%).

TABLE 4

| No. | Surfactant | Salt | Stabilizing Agent | 1 W (%) | 2 W (%) |
|---|---|---|---|---|---|
| 1 | 0.1% polysorbate 80 | 150 mM NaCl | 5% Mannitol | 95.9 | 91.8 |
| 2 | 0.01% polysorbate 80 | 150 mM NaCl | 5% Mannitol | 98.4 | 93.7 |

For the duration of the two weeks of storage, as shown in Table 4, the long-acting EPO conjugate was found to be more stable in a liquid formulation comprising 5% mannitol and 150 mM sodium chloride in 10 mM sodium phosphate buffer (pH 6.5) when it was complemented with 0.01% polysorbate 80 than with 0.1% polysorbate 80.

Example 5

Comparison of Liquid Formulations for Long-Acting EPO Conjugates (I)

With regard to storage stability, the commercially available EPO liquid formulation Recormon (Roche) was compared with the liquid formulation for long-acting EPO conjugate of the present invention. The composition of Recormon, although remaining to be proven, includes sodium phosphate as buffer, polysorbate 20 as a surfactant, sodium chloride as a salt, and urea, CaCl, glycine, leucine, isoleucine, threonine, glutamic acid and phenylalanine as stabilizing agents.

For the liquid formulations of long-acting EPO conjugates of the present invention, polysorbate 80 was used as a surfactant at various concentrations of from 0.1 to 0.005%, sodium chloride as a salt at concentrations of 150 and 200 mM, and mannitol or urea as a stabilizing agent at various concentrations of from 1 to 10% (w/v). The long-acting EPO conjugate of the present invention was stored at 40° C. for two weeks in the compositions listed in Table 5, followed by analysis by reverse phase chromatography and size exclusion chromatography (SE-HPLC). The results are summarized in Table 6, below. The retention rate of the long-acting EPO conjugate compared to the initial value thereof was expressed as RP-HPLC (%) and SE-HPLC (%).

For the two week duration of storage, as seen in Table 6, all of the liquid formulations of the present invention guaranteed higher stability of EPO than did Recormon, except formulation No. 5 having 0.1% polysorbate 80 as a surfactant and formulation No. 7 having urea as a stabilizing agent.

Example 6

Searching for Stabilizing Agents Capable of Endowing Long-Acting EPO Conjugate with Storage Stability To search for stabilizing agents which can stabilize long-acting EPO conjugates for the duration of storage over the long term, liquid formulations for long-acting EPO conjugate were prepared with the compositions of Table 7, below. In this regard, glycine and methionine were individually added to a surfactant-sodium chloride-maltose composition to examine the effect of amino acids on the long-term storage stability. In the liquid formulations, the concentration of EPO was set at 200 μg/ml in 10 mM sodium phosphate buffer (pH 6.5).

While being stored at 40° C. for four weeks, the liquid formulations for long-acting EPO conjugate were analyzed every week using reverse phase chromatography. The results are summarized in Table 8, below. The retention rate of the long-acting EPO conjugate compared to the initial value thereof was expressed as RP-HPLC (%).

TABLE 5

| No. | Name | Conc. | Buffer | Surfactant | Stabilizing Agent | Salt |
| --- | --- | --- | --- | --- | --- | --- |
| 1 | Recormon | 138 mcg/ml | Na-Phosphate | P.S 20 | Urea, CaCl, Gly, Leu, Ile, Thr, Glu, Phe | NaCl |
| 2 | Long-Acting EPO Conjugate | 200 μg/ml | 10 mM Na-Phosphate pH 6.5 | 0.005% P.S80 | 10% mannitol | 200 mM NaCl |
| 3 | Long-Acting EPO Conjugate | 200 μg/ml | 10 mM Na-Phosphate pH 6.5 | 0.005% P.S80 | 1% mannitol | 150 mM NaCl |
| 4 | Long-Acting EPO Conjugate | 200 μg/ml | 10 mM Na-Phosphate pH 6.5 | 0.01% P.S80 | 5% mannitol | 150 mM NaCl |
| 5 | Long-Acting EPO Conjugate | 200 μg/ml | 10 mM Na-Phosphate pH 6.5 | 0.1% P.S80 | 5% mannitol | 150 mM NaCl |
| 6 | Long-Acting EPO Conjugate | 200 μg/ml | 10 mM Na-Citrate pH 6.5 | 0.01% P.S80 | 5% mannitol | 150 mM NaCl |
| 7 | Long-Acting EPO Conjugate | 200 μg/ml | 10 mM Na-Phosphate pH 6.5 | 0.01% P.S80 | 25 mM Urea, 5% mannitol | 150 mM NaCl |

TABLE 6

| | RP-HPLC (%) | | | SE-HPLC (%) | | |
| --- | --- | --- | --- | --- | --- | --- |
| | Start | Week 1 | Week 2 | Start | Week 1 | Week 2 |
| 1 | 100 | 95.7 | 92.7 | 100 | 99.5 | 98.3 |
| 2 | 100 | 98.7 | | 100 | 99.3 | |
| 3 | 100 | 98.3 | 93.3 | 100 | 99.8 | 99.0 |
| 4 | 100 | 98.4 | 93.7 | 100 | 100.7 | 100.0 |
| 5 | 100 | 95.9 | 91.8 | 100 | 97.4 (tailing) | 91.5 |
| 6 | 100 | 98.8 | 93.9 | 100 | 100.7 | 100.1 |
| 7 | 100 | 98.6 | 79.0 | 100 | 100.4 | 99.5 |

TABLE 7

| No. | Surfactant | Salt | Stabilizing Agent |
| --- | --- | --- | --- |
| 1 | 0.005% polysorbate 80 | 200 mM NaCl | 10% Maltose |
| 2 | 0.005% polysorbate 80 | 200 mM NaCl | 10% Maltose + 1% glycine |
| 3 | 0.005% polysorbate 80 | 200 mM NaCl | 10% Maltose + 1 mM Methionine |

TABLE 8

| No. | RP-HPLC (%) | | | |
| --- | --- | --- | --- | --- |
|  | Week 1 | Week 2 | Week 3 | Week 4 |
| 1 | 99.12 | 94.26 | 94.27 | 70.66 |
| 2 | 97.81 | 96.60 | 95.29 | 92.43 |
| 3 | 70.14 | 57.46 | 28.34 | 15.40 |

For the duration of storage of four weeks, as shown in Table 8, the long-acting EPO conjugate was found to be the most stable in a liquid formulation comprising sodium chloride in combination with maltose and glycine as stabilizing agents. After two weeks of storage, similar storage stability was detected between the liquid formulations in which 10% maltose was used alone and in combination with 1% glycine, respectively. However, the use of 10% maltose alone significantly decreased the stability after storage for four weeks. In contrast, the use of 10% maltose in combination with 1% glycine was found to maintain high stability after storage for four weeks.

Referring to the comparison between the liquid formulations of Nos. 2 and 3, methionine significantly lowered the stability of the long-acting EPO conjugate, indicating that neutral amino acids, especially glycine, can give a great contribution to the stability of the long-acting EPO conjugate in long-term storage.

Example 7

Assay of Mannitol and Maltose for Long-Term Storage Stability of Long-Acting EPO Conjugate Three liquid formulations were prepared as given in Table 9, below: a liquid formulation comprising maltose-glycine which showed the highest stability of long-acting EPO conjugate in Example 6; the same liquid formulation, with the exception that mannitol was used instead of maltose; and a liquid formulation comprising mannitol alone. They were assayed for long-term storage stability. In the liquid formulations, the concentration of EPO was set at 200 µg/ml in 10 mM sodium phosphate buffer (pH 6.5).

While being stored at 40° C. for four weeks, the liquid formulations for long-acting EPO conjugate were analyzed every week using reverse phase chromatography. The results are summarized in Table 10, below. The retention rate of the long-acting EPO conjugate compared to the initial value thereof was expressed as RP-HPLC (%). Also, the data of Table 10 are graphed in FIG. 1 where the values of the commercially available EPO formulation Recormon are extrapolated.

TABLE 9

|  | Surfactant | Salt | Stabilizing Agent |
| --- | --- | --- | --- |
| 1 | 0.005% Polysorbate 80 | 200 mM NaCl | 10% Maltose, 1% Glycine |
| 2 | 0.005% Polysorbate 80 | 200 mM NaCl | 10% Mannitol, 1% Glycine |
| 3 | 0.005% Polysorbate 80 | 200 mM NaCl | 10% Mannitol |

TABLE 10

|  | RP-HPLC (%) | | | | |
| --- | --- | --- | --- | --- | --- |
|  | Start | Week 1 | Week 2 | Week 3 | Week 5 |
| 1 | 100 | 96.6 | 94.7 | 93.9 | 92.0 |
| 2 | 100 | 97.8 | 95.5 | 95.8 | 93.5 |
| 3 | 100 | 97.8 | 96.0 | 95.1 | 93.4 |

For the duration of storage of five weeks, as shown in Table 10, the long-acting EPO conjugate was found to be more stable in the liquid formulation comprising mannitol-glycine than maltose-glycine as stabilizing agents. Comparable storage stability was detected in the liquid formulation comprising mannitol alone.

These results are in stark contrast with the fact that the liquid formulation comprising maltose alone was significantly decreased in storage stability compared to the liquid formulation comprising maltose and glycine, indicating that mannitol can guarantee long-term storage stability to the long-acting EPO conjugate even without the aid of neutral amino acids. Also, the use of mannitol at a concentration of as high as 5 to 15% (w/v) was found to allow the EPO conjugate to be stored and retain high stability even in the absence of neutral amino acids.

Example 8

Assay of Buffer for Long-Term Storage Stability of Long-Acting EPO Conjugate

Buffers were assayed for ability to stabilize the long-acting EPO conjugate. Also, an examination was made of the relationship between the stability of long-acting EPO conjugates and the doses of salts and sugar alcohols, as follows.

First, the effects of buffers on the stability of long-acting EPO conjugates were investigated using liquid formulations which were formulated with 0.01% polysorbate, 150 mM sodium chloride, and phosphate or citrate buffer as shown in Table 11 (No. 1 and 2). The liquid formulations contained a high concentration (5%) of mannitol as a stabilizing agent, but not any amino acids, and the long-acting EPO conjugate was added at a concentration of 200 µg/ml. The formulations were stored at 40° C. for four weeks, during which time the liquid formulations for long-acting EPO conjugate were analyzed Week 1 and Week 4 using reverse phase chromatography. The results are summarized in Table 12 (No. 1 and 2), below. The retention rate of the long-acting EPO conjugate compared to the initial value thereof was expressed as RP-HPLC (%).

The same liquid formulation comprising mannitol as in Example 7, the same liquid formulation but comprising citrate buffer instead of phosphate buffer, and the same liquid formulation but comprising half of the amounts of the salt and the sugar alcohol were examined for their effect on the stability of the long-acting EPO conjugate.

In the liquid formulations, the concentration of the long-acting EPO conjugate was set at 200 µg/ml and the stabilizing agents were used as shown in Table 11, below. The liquid formulations for long-acting EPO conjugate were stored at 40° C. and analyzed Week 1 and Week 4 using reverse phase chromatography. The results are summarized in Table 12, below. The retention rate of the long-acting EPO conjugate compared to the initial value thereof was expressed as RP-HPLC (%).

TABLE 11

| No. | Buffer | Surfactant | Salt | Stabilizing Agent |
|---|---|---|---|---|
| 1 | 10 mM Na-Phosphate, pH 6.5 | 0.01% Polysorbate80 | 150 mM NaCl | 5% Mannitol |
| 2 | 10 mM Na-Citrate, pH 6.5 | 0.01% Polysorbate80 | 150 mM NaCl | 5% Mannitol |
| 3 | 10 mM Na-Phosphate, pH 6.5 | 0.005% Polysorbate80 | 200 mM NaCl | 10% Mannitol |
| 4 | 10 mM Na-Citrate, pH 6.0 | 0.01% Polysorbate80 | 100 mM NaCl | 5% Mannitol |

TABLE 12

| | RP-HPLC (%) | | |
|---|---|---|---|
| | Start | Week 1 | Week 4 |
| 1 | 100 | 98.4 | 93.7 |
| 2 | 100 | 98.8 | 93.9 |
| 3 | 100 | 98.7 | 94.3 |
| 4 | 100 | 99.5 | 95.0 |

As is apparent from the data of Table 12, the liquid formulations, if they contained mannitol therein, guaranteed the storage stability of the long-acting conjugate at the desired levels irrespective of the kinds of the buffers used therein. These results indicate that typical buffers other than phosphate buffer can be used to prepare liquid formulations in which the long-acting EPO conjugate can be stored stably for a long period of time.

Example 9

Comparison of Storage Stability of Long-Acting EPO Conjugates between Liquid Formulations (II)

With regard to storage stability, the liquid formulation which was prepared with phosphate buffer (pH 6.5), sodium chloride, mannitol and polysorbate 80, all proven for stabilizing ability in Examples 2 to 8, was compared with the commercially available EPO liquid formulation Recormon, Roche. The compositions of the liquid formulation of the present invention and Recormon are shown in Table 13, below. While being stored at 40° C. for four weeks, the liquid formulations for long-acting EPO conjugate were analyzed Week 2 and Week 4 using reverse phase chromatography and size exclusion chromatography. The results are summarized in Table 14, below. The retention rate of the long-acting EPO conjugate compared to the initial value thereof was expressed as RP-HPLC (%) and SE-HPLC (%).

TABLE 13

| Name | Conc. | Buffer | Surfactant | Salt | Stabilizing Agent |
|---|---|---|---|---|---|
| Recormon | EPO 138 mcg/mL | Na-Phosphate | Polysorbate 20 | NaCl | Urea, CaCl, Gly, Leu, Ile, Thr, Glu, Phe |
| Long-Acting EPO | EPO 200 mcg/mL | 10 mM Na-Phosphate (pH 6.5) | 0.005% Polysorbate 80 | 200 mM NaCl | 10% Mannitol |

TABLE 14

| | RP-HPLC (%) | | | SE-HPLC (%) | | |
|---|---|---|---|---|---|---|
| Name | Start | Week 2 | Week 4 | Start | Week 2 | Week 4 |
| Recormon | 100 | 96.1 | 91.6 | 100 | 98.4 | 93.1 |
| Long-acting EPO | 100 | 95.5 | 93.3 | 100 | 98.1 | 96.4 |

As is apparent from the data of Table 14, the liquid formulation containing a high concentration of mannitol as a stabilizing agent guaranteed greater storage stability of EPO than Recormon that contained various kinds of neutral amino acids. From these results, it is understood that the liquid formulations of the present invention are capable of guaranteeing excellent storage stability specifically to the long-acting EPO conjugate.

Example 10

Comparison of Storage Stability Among Various Liquid Formulations

With regard to storage stability, a liquid formulation which was prepared with phosphate buffer (pH 6.5), sodium chloride, mannitol and polysorbate 80, all proven for the stabilizing ability shown in Examples 2 to 8, was compared with the liquid formulations which were prepared by applying the compositions of various commercially available formulations to the long-acting EPO conjugate.

Liquid formulations used in this example are summarized in Table 15, below. In Table 15, No. 1 is Aranesp, manufactured by Amgen, that is currently used as an anemia therapeutic; No. 2 is a liquid formulation which was prepared with a stabilization composition comprising phosphate buffer (pH 6.5), sodium chloride, mannitol and polysorbate 80; No. 3 is the same liquid formulation as in Aranesp, with the exception that the long-acting EPO conjugate was used instead of the drug; No. 4 is the same liquid formulation as in Enbrel (TNFR-Fc), a therapeutic for rheumatoid arthritis manufactured by Amgen, with the exception that the long-acting EPO conjugate was used instead of the drug; and No. 5 is a liquid formulation containing PBS alone.

While being stored at 40° C. for three weeks, the liquid formulations for long-acting EPO conjugate were analyzed every week using reverse phase chromatography and size exclusion chromatography. The results are summarized in Table 17, below. The retention rate of the long-acting EPO conjugate compared to the initial value thereof was expressed as RP-HPLC (%) and SE-HPLC (%).

TABLE 15

| | Protein | Conc. | Buffer | Surfactant | Stabilizing Agent | Salt |
|---|---|---|---|---|---|---|
| 1 | Aranesp | 200 μg/ml | 20 mM Na-Phosphate (pH 6.2) | 0.005% P.S 80 | — | 140 mM NaCl |
| 2 | Long-Acting EPO Conjugate | 0.526 mg/ml | 10 mM Na-Phosphate (pH 6.5) | 0.005% P.S 80 | 10% Mannitol | 200 mM NaCl |
| 3 | Long-Acting EPO Conjugate | 0.526 mg/ml | 20 mM Na-Phosphate (pH 6.2) | 0.005% P.S 80 | — | 140 mM NaCl |
| 4 | Long-Acting EPO Conjugate | 0.526 mg/ml | 25 mM Na-Phosphate (pH 6.3) | | 1% Sucrose 25 mM L-arginine hydrochloride | 100 mM NaCl |
| 5 | Long-Acting EPO Conjugate | 0.526 mg/ml | PBS | | | |

TABLE 16

| | |
|---|---|
| Batch Number | HM10760A B10098 LGL211 (Research Center batch) |
| Temperature | 40° C. |
| Storage Condition | Glass Syringe, 500 μl |
| Analysis Method | SEC, RPC |
| Sample Frequency | Start, 1 W, 2 W, 3 W |

TABLE 17

| | | | Start | 1 W | 2 W | 3 W |
|---|---|---|---|---|---|---|
| 1 | Aranesp | SEC (Area %) | 99.7 | 99.4 | 98.6 | Aggregated |
| | | SEC (Area %/Initial Area %) % | 100.0 | 99.7 | 98.9 | |
| | | SEC (Area/Initial Area) % | 100.0 | 100.1 | 99.8 | |
| | | RPC (Area %) | 94.0 | 92.5 | 91.6 | |
| | | RPC (Area %/Initial Area %) % | 100.0 | 98.4 | 97.4 | |
| | | RPC (Area/Initial Area) % | 100.0 | 99.9 | 98.7 | |
| 2 | Long-Acting EPO Conjugate | SEC (Area %) | 98.8 | 97.8 | 96.6 | 91.6 |
| | | SEC (Area %/Initial Area %) % | 100.0 | 99.0 | 97.8 | 92.7 |
| | | SEC (Area/Initial Area) % | 100.0 | 97.3 | 92.1 | 88.9 |
| | | RPC (Area %) | 96.0 | 92.6 | 87.9 | 83.9 |
| | | RPC (Area %/Initial Area %) % | 100.0 | 96.5 | 91.6 | 87.4 |
| | | RPC (Area/Initial Area) % | 100.0 | 94.4 | 89.9 | 85.4 |
| 3 | Long-Acting EPO Conjugate | SEC (Area %) | 98.8 | 98.0 | 96.7 | Aggregated |
| | | SEC (Area %/Initial Area %) % | 100.0 | 99.2 | 97.9 | |
| | | SEC (Area/Initial Area) % | 100.0 | 96.3 | 91.2 | |
| | | RPC (Area %) | 95.0 | 92.3 | 87.5 | |
| | | RPC (Area %/Initial Area %) % | 100.0 | 97.2 | 92.1 | |
| | | RPC (Area/Initial Area) % | 100.0 | 95.3 | 91.4 | |
| 4 | Long-Acting EPO Conjugate | SEC (Area %) | 98.9 | 96.5 | Aggregated | Aggregated |
| | | SEC (Area %/Initial Area %) % | 100.0 | 97.6 | | |
| | | SEC (Area/Initial Area) % | 100.0 | 94.2 | | |
| | | RPC (Area %) | 94.4 | 90.8 | | |
| | | RPC (Area %/Initial Area %) % | 100.0 | 96.2 | | |
| | | RPC (Area/Initial Area) % | 100.0 | 93.3 | | |
| 5 | Long-Acting EPO Conjugate | SEC (Area %) | 98.8 | 97.4 | Aggregated | Aggregated |
| | | SEC (Area %/Initial Area %) % | 100.0 | 98.6 | | |
| | | SEC (Area/Initial Area) % | 100.0 | 96.5 | | |
| | | RPC (Area %) | 94.6 | 91.6 | | |
| | | RPC (Area %/Initial Area %) % | 100.0 | 96.8 | | |
| | | RPC (Area/Initial Area) % | 100.0 | 95.5 | | |

As is apparent from the date of Table 17, all the liquid formulations, but the liquid formulation comprising 10 mM sodium phosphate buffer (pH 6.5), 0.005% polysorbate 80, 10% mannitol and 200 nM sodium chloride in accordance with the present invention, were observed to aggregate during storage over the course of the three weeks. Consequently, the liquid formulation comprising 10 mM sodium phosphate buffer (pH 6.5), 0.005% polysorbate 80, 10% mannitol and 200 nM sodium chloride in accordance with the present invention is the most promising agent for storing the long-acting EPO conjugate stably for a long period of time.

Example 11

Figure 2:
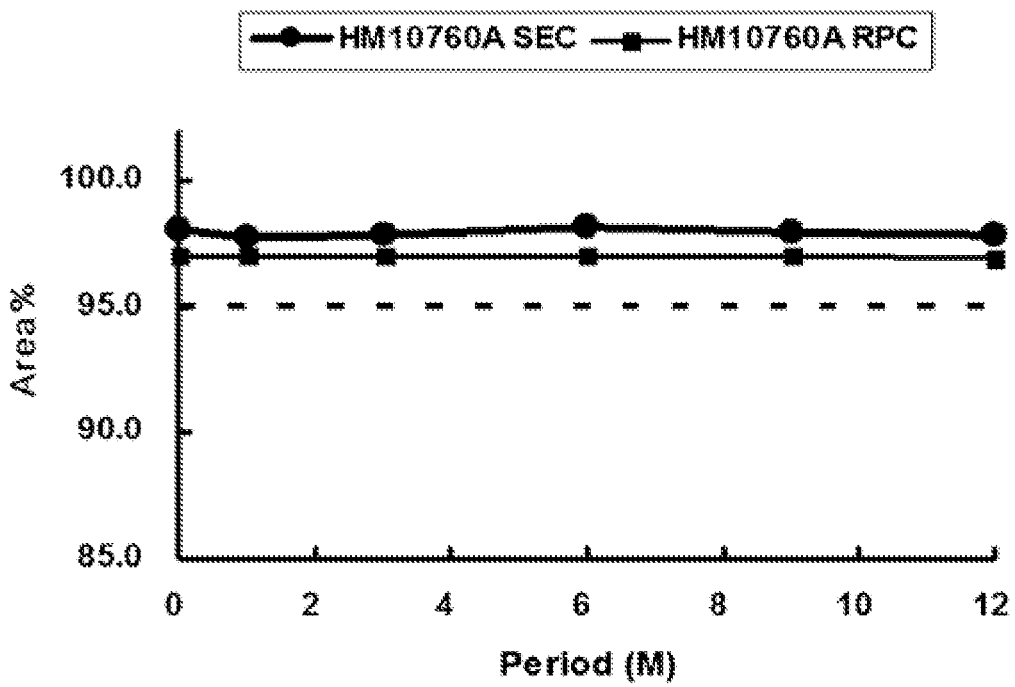
FIG. 2 is a graph showing the stability of the long-acting EPO conjugate in a liquid formulation comprising phosphate buffer pH 6.5, sodium chloride, mannitol and polysorbate 80 when it was analyzed using reverse-phase chromatography and size exclusion chromatography every two months for the duration of storage at 4° C. for 12 months.

Assay of Liquid Formulations for Long-Acting EPO Conjugate for Long-Term Storage Stability and Accelerated Stability To examine the long-term storage stability and accelerated stability thereof, the liquid formulation for long-acting EPO conjugate, prepared from a stabilizer comprising phosphate buffer (pH 6.5), sodium chloride, mannitol and polysorbate 80, which was proven to guarantee the most storage stability, was stored at 4° C. for 12 months over which the stability of the long-acting EPO conjugate was analyzed. Detailed conditions for storage are summarized in Table 18, below. Analysis results are given in Table 19 and FIG. 2. In Table 19, the retention rate of the long-acting EPO conjugate compared to the initial value thereof was expressed as RP-HPLC (%) and SE-HPLC (%).

Figure 3:
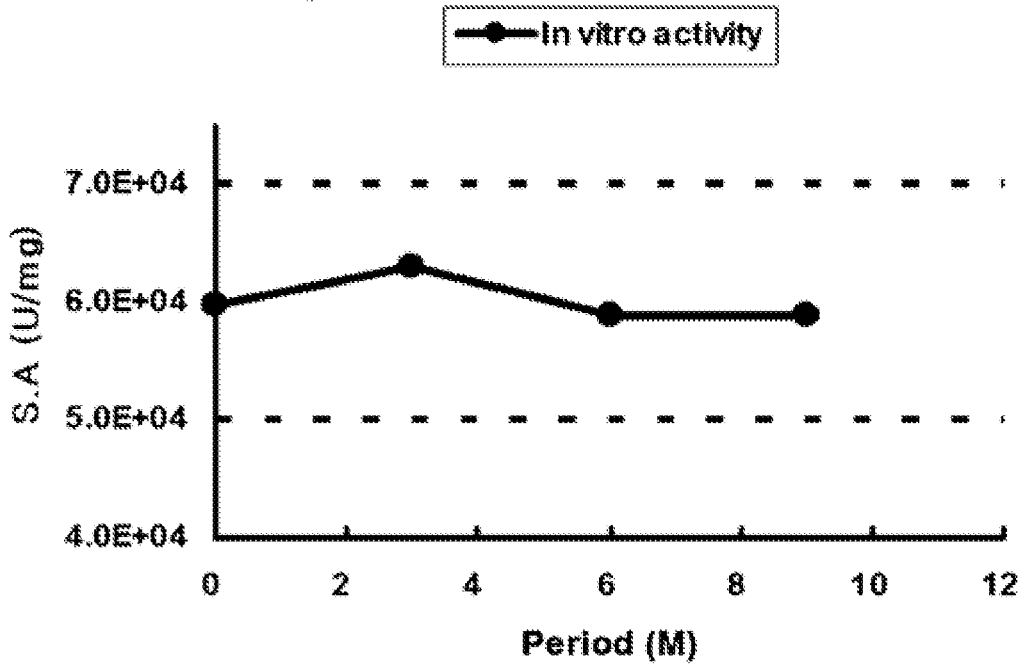
FIG. 3 is a graph showing the stability of the long-acting EPO conjugate in a liquid formulation comprising phosphate buffer pH 6.5, sodium chloride, mannitol and polysorbate 80 when it was analyzed using an in vitro assay every two months for the duration of storage at 4° C. for 12 months.

In addition, the liquid formulation for long-acting EPO conjugate was in vitro assayed for storage stability for the duration of storage at 4° C. for 12 months (FIG. 3).

The long-acting EPO conjugate used in this Example was in vitro measured for tite in a TF-1 cell line (erythroleukemia cell, ATCC CRL 2003). After being thawed from a storage nitrogen tank, TF-1 cells were cultured to a predetermined extent and counted. A mixture of BRP-EPO and the long-acting EPO conjugate at a predetermined ratio was plated in an amount of 50 µL/well into 96-well plates. The cells were diluted at a concentration of 40000 cells/mL in an assay medium which was then seeded in an amount of 50µ/well into the 96-well plates. Following incubation at 37° C. for 72 hrs in a $CO_2$ incubator, 15 µL of CellTiter 96 Aqueous One Solution Reagent (PROMEGA, G358B) was added to each well of the 96-well plates. They were incubated again at 37° C. for 4 hrs in a $CO_2$ incubator. The staining reagent was removed by gently pippetting, followed by the measurement of absorbance at 490 nm to calculate EC50. Specific activity was obtained from the calculated EC50 values.

TABLE 18

| | |
|---|---|
| Batch Number | HM10760A B10098 LGL071 |
| Concentration | 0.352 mg/ml protein |
| Temperature | 4° C. |
| Storage condition | Glass syringe 500 ml |
| Analysis method | SEC, RPC |
| Formulation | 10 mM Na—P (pH 6.5)/0.005% Polysorbate 80/10% Mannitol/200 mM NaCl |
| Sampling frequency | Start, 1M, 3M, 6M, 9M, 12M, |

TABLE 19

| | | Start | 1M | 3M | 6M | 9M | 12M |
|---|---|---|---|---|---|---|---|
| Long-Acting EPO Conjugate-Storage at 4° C. | SEC (Area %) | 98.1 | 97.8 | 97.9 | 98.2 | 98.0 | 97.9 |
| | SEC (Area %/Initial Area %) % | 100.0 | 99.7 | 99.8 | 100.1 | 99.9 | 99.8 |
| | SEC (Area/Initial Area) % | 100.0 | 97.5 | 89.7 | 91.8 | 92.2 | 92.6 |
| | RPC (Area %) | 97.1 | 97.1 | 97.1 | 97.1 | 97.1 | 97.0 |
| | RPC (Area %/Initial Area %) % | 100.0 | 100.0 | 100.0 | 100.0 | 100.0 | 99.9 |
| | RPC (Area/Initial Area) % | 100.0 | 100.4 | 98.3 | 99.2 | 99.3 | 99.7 |
| | Specific Activity (U/mg) | 5.97E+04 | — | 6.31E+04 | 5.90E+04 | 5.88E+04 | |
| | VS Start (%) | 100.0 | — | 105.8 | 98.8 | 98.5 | |

As shown in Table 19, the long-acting EPO conjugate was found to be very stable for 12 months in the liquid formulation comprising the stabilizer composition of the present invention.

Further, as mentioned above, the liquid formulation for long-acting EPO conjugate, comprising the same stabilizer composition, was stored at 4° C. for 12 months and subsequently at 25° C. for 6 months during which samples were analyzed for storage stability. The results are summarized in Tables 20 and 21, below. In Tables 20 and 21, the retention rate of the long-acting EPO conjugate compared to the initial value thereof was expressed as RP-HPLC (%), SE-HPLC (%), protein content (%) and biological inert activity (%).

TABLE 20

Assay for Long-Term Storage Stability (Storage at 4° C.)

| Storage Term | Properties | pH | Identification Test | | | Purity Test | | Protein Content Test (%) | Biological Inert Activity (%) |
|---|---|---|---|---|---|---|---|---|---|
| | | | HPLC | Western Blot | SDS-PAGE | RP-HPLC (%) | SE-HPLC (%) | | |
| Start | Colorless transparent | 6.3 | Agreed | Suitable | Suitable | 100.0 | 100.0 | 100.0 | 100.0 |
| 3 Months | Colorless transparent | 6.5 | Agreed | Suitable | Suitable | 100.0 | 101.1 | 100.0 | 122.7 |
| 6 Months | Colorless transparent | 6.4 | Agreed | Suitable | Suitable | 99.5 | 101.0 | 98.3 | 121.2 |
| 9 Months | Colorless transparent | 6.4 | Agreed | Suitable | Suitable | 99.3 | 101.1 | 103.9 | 131.1 |
| 12 Months | Colorless transparent | 6.5 | Agreed | Suitable | Suitable | 99.1 | 100.1 | 99.2 | 124.4 |

TABLE 21

Accelerated Stability Assay (Storage at 25° C.)

| Storage Term | Properties | pH | Identification Test | | | Purity Test | | Protein Content Test (%) | Biological Inert Activity (%) |
|---|---|---|---|---|---|---|---|---|---|
| | | | HPLC | Western Blot | SDS-PAGE | RP-HPLC (%) | SE-HPLC (%) | | |
| Start | Colorless transparent | 6.3 | Agreed | Suitable | Suitable | 100.0 | 100.0 | 100.0 | 100.0 |
| 2 Months | Colorless transparent | N.A | Agreed | Suitable | Suitable | 97.6 | 99.7 | N.A | 91.3 |
| 4 Months | Colorless transparent | N.A | Agreed | Suitable | Suitable | 96.2 | 99.7 | N.A | 106.4 |
| 6 Months | Colorless transparent | 6.5 | Agreed | Suitable | Suitable | 92.5 | 94.0 | 100.0 | 101.5 |

As is apparent from the data of Tables 20 and 21, the long-acting EPO conjugate was kept highly stable for 12 months in the liquid formulation comprising the stabilizer composition according to the present invention and was found to have 92.5% of the initial activity even after having been stored for 6 months in the liquid formulation under the accelerated condition. Therefore, the liquid formulation for long-acting EPO conjugate according to the present invention exhibits effective storage stability.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

Being free of human serum albumin, the liquid formulation for guaranteeing storage stability specifically to long-acting erythropoietin conjugates in accordance with the present invention is freed from concerns about viral infections. It comprises a simple composition, thus having an economical advantage over other stabilizers or freeze-dryer formulations. In addition, because it contains a long-acting EPO conjugate which has a longer duration of action than does a natural form and also keeps the protein activity high for a long period of time, the liquid formulation can be used as an effective drug system.

The invention claimed is:

1. A liquid formulation consisting of a therapeutically effective amount of a long-acting erythropoietin (EPO) conjugate, mannitol, a buffer, a salt, and a polysorbate-based non-ionic surfactant,
   wherein the EPO is covalently linked to an immunoglobulin Fc fragment via a non-peptide polymer or peptide linker,
   wherein mannitol is included at a concentration from 5 to 20% (w/v),
   wherein the liquid formulation does not comprise a neutral amino acid and albumin, and
   wherein the buffer is a sodium phosphate buffer or a sodium citrate buffer.

2. The liquid formulation according to claim 1, wherein an amount of the buffer ranges from 5 to 100 mM.

3. The liquid formulation according to claim 1, wherein the pH of the buffer ranges from 4 to 8.

4. The liquid formulation according to claim 1, wherein the salt is selected from the group consisting of sodium chloride, sodium sulfate, sodium citrate and a combination thereof.

5. The liquid formulation according to claim 1, wherein the salt ranges in a concentration from 5 to 200 mM.

6. The liquid formulation according to claim 1, wherein the polysorbate-based non-ionic surfactant is selected from the group consisting of polysorbate 20, polysorbate 40, polysorbate 60 and polysorbate 80.

7. The liquid formulation according to claim 1, wherein the non-ionic surfactant ranges in a concentration from 0.001 to 0.05% (w/v) based on the total volume of the liquid formulation.

8. The liquid formulation according to claim 1, wherein the buffer is a sodium phosphate buffer at a concentration from 5 to 100 mM, the salt is sodium chloride at a concentration from 5 to 200 mM, and the polysorbate-based non-ionic surfactant is polysorbate 80 at a concentration from 0.001 to 0.05% (w/v).

9. The liquid formulation according to claim 1, wherein the EPO is a mutant EPO protein modified from the wild-type EPO by substitution, deletion or insertion of an amino acid or amino acids, or a peptide analogue having activity similar to that of the wild-type EPO.

10. The liquid formulation according to claim 1, wherein the EPO ranges in a concentration from 1 to 500 µg/ml.

11. The liquid formulation according to claim 1, wherein the immunoglobulin Fc fragment is selected from the group consisting of IgG, IgA, IgD, IgE, IgM and a combination thereof.

12. The liquid formulation according to claim 11, wherein the immunoglobulin Fc fragment is a hybrid fragment composed of domains of different origins from the group consisting of IgG, IgA, IgD, IgE and IgM.

13. The liquid formulation according to claim 11, the immunoglobulin Fc fragment is in a form of a dimer or a multimer of single-chain immunoglobulins composed of domains of the same origin.

14. The liquid formulation according to claim 11, wherein the immunoglobulin Fc fragment is an IgG4 Fc fragment.

15. The liquid formulation according to claim 14, wherein the immunoglobulin Fc fragment is a human aglycosylated IgG4 Fc fragment.

16. The liquid formulation according to claim 1, wherein the non-peptide polymer is selected from the group consisting of a biodegradable polymer, a lipid polymer, chitin, hyaluronic acid, and a combination thereof.

17. The liquid formulation according to claim 16, wherein the biodegradable polymer is selected from the group consisting of polyethylene glycol, polypropylene glycol, a copolymer of ethylene glycol and propylene glycol, polyoxyethylated polyols, polyvinyl alcohol, polysaccharides, dextran, polyvinyl ethylether, polylactic acid and polylactic-glycolic acid.

* * * * *